United States Patent
Essenpreis et al.

(10) Patent No.: US 10,299,737 B2
(45) Date of Patent: *May 28, 2019

(54) SYSTEM, TOOLS, DEVICES AND A PROGRAM FOR DIABETES CARE

(75) Inventors: Matthias Essenpreis, Weinheim (DE); Michael Schoemaker, Mannheim (DE); Sebastiaan La Bastide, Muri bei Bern (CH); Derek Brandt, Oberdorf (CH); Theodor Koschinsky, Dusseldorf (DE); Sascha Heckermann, Haan (DE)

(73) Assignee: Roche Diabetes Care, Inc, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/786,993

(22) Filed: May 25, 2010

(65) Prior Publication Data
US 2010/0235316 A1  Sep. 16, 2010

Related U.S. Application Data

(63) Continuation of application No. 12/044,133, filed on Mar. 7, 2008, now Pat. No. 7,766,831, which is a (Continued)

(30) Foreign Application Priority Data

Sep. 9, 2005  (CH) ...................... 1468/05

(51) Int. Cl.
  *A61B 5/00* (2006.01)
  *G06F 19/00* (2018.01)
  *A61B 5/145* (2006.01)
(52) U.S. Cl.
  CPC ............ *A61B 5/743* (2013.01); *A61B 5/7275* (2013.01); *A61B 5/7445* (2013.01); *G06F 19/00* (2013.01); *A61B 5/14532* (2013.01)

(58) Field of Classification Search
  CPC .................... A61B 5/7275; A61B 5/14532
  (Continued)

(56) References Cited

U.S. PATENT DOCUMENTS

| | | |
|---|---|---|
| 3,939,640 A | 2/1976 | Kahn |
| 5,791,344 A | 8/1998 | Schulman et al. |

(Continued)

FOREIGN PATENT DOCUMENTS

| | | |
|---|---|---|
| EP | 1 281 351 | 2/2003 |
| WO | WO 20030030731 | 4/2003 |

OTHER PUBLICATIONS

FDA Approval order GlucoWatch Automatic Glucose Biographer—P990026, http://www.fda.gov/MedicalDevices/ProductsandMedicalProcedures/DeviceApprovalsandClearances/Recently-ApprovedDevices/ucm089158.htm Retrieved from the Internet on Aug. 25, 2010. 1 pg.

(Continued)

*Primary Examiner* — Christian Jang
(74) *Attorney, Agent, or Firm* — Dinsmore & Shohl LLP

(57) ABSTRACT

A method for diabetes care, the method (which also may be referred to as, involve or incorporate at least one of a tool, device or program) allowing for the characterization of the relevance of errors of parameters affecting glucose concentration on a postprandial glucose concentration outcome for a person with diabetes mellitusm, wherein the method involves at least one of sensing, determining, calculating, predicting, describing and communicating the effects of potential errors of parameters affecting glucose concentration on postprandial glucose concentration values within a clinically relevant glucose range.

15 Claims, 11 Drawing Sheets

---

MODEL PARAMETERS

A) BLOOD GLUCOSE (BG) MEASUREMENT (PREPRANDIAL) BY SMBG
B) EFFECT OF CARBOHYDRATE-PORTION (CARB-P) ON MAXIMUM BG INCREASE
C) PATIENT ESTIMATE OF CARBOHYDRATE AMOUNT IN MEALS
D) EFFECT OF S.C. PRANDIAL INSULIN ON MAX. BG DECREASE
E) INSULIN DOSAGE

Related U.S. Application Data continuation of application No. PCT/CH2006/000483, filed on Sep. 8, 2006.

(58) Field of Classification Search
USPC .................. 600/316, 319, 345–347, 365
See application file for complete search history.

(56) References Cited

U.S. PATENT DOCUMENTS

| | | |
|---|---|---|
| 7,254,516 B2 * | 8/2007 | Case et al. .................. 702/182 |
| 2001/0016682 A1 | 8/2001 | Berner et al. |
| 2002/0019707 A1 | 2/2002 | Cohen et al. |
| 2003/0028089 A1 * | 2/2003 | Galley et al. ................ 600/365 |
| 2005/0027180 A1 * | 2/2005 | Goode et al. ................ 600/365 |
| 2005/0114062 A1 | 5/2005 | Davies et al. |
| 2006/0020186 A1 * | 1/2006 | Brister et al. ................ 600/345 |
| 2007/0287596 A1 | 12/2007 | Case, Jr. et al. |

OTHER PUBLICATIONS

Feldman et al.. A Continuous Glucose Sensor Based on Wired Enzyme Technology. Diabetes Technology & Therapeutics, 5, 5, 769-779, 2003.

Mastrototaro J. The MiniMed Continuous Glucose Monitoring System. Journal of Pediatric Endocronology & Metabolism, 12, 751-758 (1999)].

Parkes et al. "A new consensus Error Grid to evaluate the clinical significance of inaccuracies in the measurement of blood glucose", Diabetes Care, 23: 8:1143-1148, Aug. 2000.

\* cited by examiner

MODEL PARAMETERS

A) BLOOD GLUCOSE (BG) MEASUREMENT (PREPRANDIAL) BY SMBG
B) EFFECT OF CARBOHYDRATE-PORTION (CARB-P)
   ON MAXIMUM BG INCREASE
C) PATIENT ESTIMATE OF CARBOHYDRATE AMOUNT IN MEALS
D) EFFECT OF S.C. PRANDIAL INSULIN ON MAX. BG DECREASE
E) INSULIN DOSAGE

Fig. 2

| ME | a<br>BG MEASUREMENT % | b<br>CARB-P BG INCREASE mg/dl | c<br>CARB ESTIMATE % | d<br>INSULIN BG DECREASE mg/dl | e<br>1 IU INSULIN % |
|---|---|---|---|---|---|
| HIGHEST | +50% | 80 | 200% | 50 | +50% |
| NO ERROR | 0% | 40 | 100% | 40 | 0% |
| LOWEST | -50% | 20 | 40% | 30 | -25% |

Fig. 3

CRITICAL POINTS (CP) OF PARAMETER ERRORS

| PARAMETERS AFFECTING BG | CP HYPOGLYCEMIA Δ FROM MEAN (IDEAL) | CP HYPERGLYCEMIA Δ FROM MEAN (IDEAL) |
|---|---|---|
| a) SMBG TEST | +12% | -41% |
| b) BG↑ EFFECT/CARB-P | -10% | +20% |
| c) ESTIMATE/CARB-P | +12% | -20% |
| d) BG↓ EFFECT/ IU INSULIN | +10% | -20% |

Fig. 9

SYSTEM, TOOLS, DEVICES AND A PROGRAM FOR DIABETES CARE

CROSS REFERENCE TO RELATED APPLICATIONS

This application is a continuation of U.S. patent application Ser. No. 12/044,133, filed Mar. 7, 2008, which is a continuation of International Patent Application No. PCT/CH2006/000483, filed on Sep. 8, 2006, which claims priority to Swiss Application No. 1468/05, filed on. Sep. 9, 2005, the contents of which are hereby incorporated in their entirety by reference herein.

BACKGROUND

The present invention relates to the treatment or therapeutic care of diabetes, to devices for use in diabetes care, and to methods of making and using such devices, and to methods of treatment or care of diabetes. In some embodiments, the present invention relates to at least one of a system, a diagnostic tool, a therapeutic tool and an educational tool for diabetes self-management. In some embodiments, the present invention relates to a medical device for use in diabetes care, e.g. a blood glucose meter, an insulin pump or a continuous glucose monitoring device. In some embodiments, the present invention relates to program, method or process for diabetes management, and to a data carrier including such a program.

Considerable progress has been made in the development of diagnostic, therapeutic and educational tools for diabetes self-management. However, it is less recognized that in the daily life of people with diabetes mellitus all such tools are characterized by rather large and varying margins of error. There exists insufficient knowledge about the effects of such errors on postprandial blood glucose and, thus, about their contribution to the increases risk of hypoglycemia and hyperglycemia.

Some currently known systems, and in particular systems for continuous glucose monitoring, do not display actual results to avoid a possibly false therapy decision based on an uncertain measuring value (a value with a measuring error that could be too large). With such systems only a retrospective analysis of the measured values is possible. [Mastrototaro J. The MiniMed Continuous Glucose Monitoring System. Journal of Pediatric Endocronology & Metabolism, 12, 751-758 (1999)].

Other systems for continuously monitoring glucose do display actual measurement values, but are not approved for therapy decisions. For such decisions it is in both cases necessary to measure the blood glucose value with strip measurement devices. [FDA Approval order GlucoWatch Automatic Glucose Biographer-P990026, http://www.fda.gov/cdrh/pdf/p990026.html].

According to the manufacturer's information a system for continuous glucose monitoring shall be able to allow therapy decision without confirmaton by a conventional measuring system. [Feldman B, Brazg R, Schwartz S, Weinstein R. A Continuous Glucose Sensor Based on Wired Enzyme Technology. Diabetes Technology & Therapeutics, 5, 5, 769-779, 2003].

SUMMARY

One object of the present invention is to provide a system that allows a person with diabetes or a medical practioner or caregiver to predict a postprandial blood glucose value. Another object of the present invention is to provide a model for explaining the impacts of errors of measurements and estimations in diabetes treatment and diabetes self care. Another object of the present invention is to provide devices that allow a more precise prediction of postprandial blood glucose and, thus, can give valid treatment information and/or advice.

To implement these and other objects of the present invention, which will become more readily apparent as the description proceeds, the present invention is manifested by a system for determining postprandial blood glucose taking into account factors or variables in the treatment of diabetes, including one or more of the following:

preprandial blood glucose measurement by self-monitoring of glucose,
the effect of carbohydrate-portion on maximum glucose incrase,
an estimate of carbohydrate amount in meal,
the effect of preprandial insulin on maximum glucose decrease, and
insulin dosage, wherein a margin of error for self-monitored preprandial glucose is taken into account and postprandial glucose values are calculated based on a therapeutic action scheme.

In one embodiment, the present invention comprises a method (which also may be referred to as, involve or incorporate a system, tool, device or program) for diabetes care, the method allowing for the characterization of the relevance of errors of parameters affecting glucose concentration on a postprandial glucose concentration outcome for a person with diabetes mellitusm, wherein the method involves at least one of sensing, determining, calculating, manipulating, predicting, describing and communicating the effects of potential errors of parameters affecting glucose concentration on postprandial glucose concentration values within a clinically relevant glucose range.

In one embodiment, the present invention comprises a method of therapy, diagnosis or education involving postprandial glucose concentration, said method comprising the step of taking into account at least one of a preprandial glucose measurement by self-monitoring of glucose concentration, an effect of carbohydrate-portion on maximum glucose increase, an estimate of carbohydrate amount in a meal, an effect of prandial insulin on maximum glucose decrease, and an insulin dosage, wherein a margin of error for self-monitored preprandial glucose is taken into account and postprandial glucose values are calculated based on a therapeutic action scheme. In some embodiments, the invention may further comprise the step of taking into account an error associated with at least one of the effect of carbohydrate-portion on maximum glucose increase, the estimate of carbohydrate amount in a meal, the effect of prandial insulin on maximum glucose decrease, and the insulin dosage. In some embodiments, the invention may comprise determining the postprandial blood glucose for different ranges of preprandial glucose concentration values according to the therapeutic scheme, and communicating a result as postprandial glucose over preprandial glucose. In some embodiments, it is determined whether a critical point is reached by exceeding a lower limit for glucose concentration or by exceeding an upper limit for glucose concentration.

In some embodiments of the methods in accordance with the present invention, the therapeutic scheme includes a carbohydrate self-adjustment in relation to preprandial glucose concentration according to the relation:
Glucose (mg/dl)<40 40-60 61-120 121-160 161-200 201-240 241-300 301-360 CARB-P (n) X+2 X+1 X X-1 X-2

X-3 X-4 X-5 wherein X equals the number of carbohydrate portions (X=1, 2, 3, 4 or 5) for the glucose-range of 61-120 mg/dl.

In some embodiments, the method comprises a therapeutic scheme includes a pre-prandial insulin dose self-adjustment according to the relation:
BG (mg/dl)<61 61-80 81-120 121-160 161-200 201-240 241-300 301-360 Ins.-Dose (U) 0 -1Y Y +1Y +2Y +3Y +4Y +5Y wherein Y equals e.g. 1 unit insulin per 1 CARB-P for the blood glucose range of 81-120 mg/dl.

In some embodiments, the trend of a continuous glucose monitoring is considered as follows:

|       | Glucose (mg/dl) | | | | | | | |
|-------|-----|-------|--------|---------|---------|---------|---------|---------|
| Trend | <61 | 61-80 | 81-120 | 121-160 | 161-200 | 201-240 | 241-300 | 301-360 |
| UU    | 0   | Y     | +1Y    | +2Y     | +3Y     | +4Y     | +5Y     | +6Y     |
| U     | 0   | -1Y   | Y      | +1Y     | +2Y     | +3Y     | +4Y     | +5Y     |
| =     | 0   | -1Y   | Y      | +1Y     | +2Y     | +3Y     | +4Y     | +5Y     |
| D     | 0   | -2Y   | -1Y    | Y       | +1Y     | +2Y     | +3Y     | +4Y     |
| DD    | 0   | -3Y   | -2Y    | -1Y     | Y       | +1Y     | +2Y     | +3Y     | and wherein the trends are defined as follows

| Very Fast glucose increase | >+2 mg/dl/min | UU |
| Fast | +(1-2) mg/dl/min | U |
| Slow changes | <±1 mg/dl/min | = |
| Fast decrease | -(1-2) mg/dl/min | D |
| Very Fast decrease | >-2 mg/dl/mim | DD |

In some embodiments of the method in accordance with the present invention, the method may involve or be carried out or performed by or in conjunction with at least one of a blood glucose meter, an insulin pump or a continuous glucose monitor.

In some embodiments, the system or tool (or method) of the present invention has been developed and/or is adapted to evaluate the effects and the clinical relevance of the margins of error of parameters affecting glucose. In some embodiments, it is based on a diabetes treatment concept aimed at normoglycemia after meals by preprandial injections of insulin. The system or tool includes as parameters one or more of: a) preprandial measurement, b) effect of carbohydrate portions (CARE-P) on maximum glucose increase, c) patient estimate of carbohydrate amounts in food, d) effect of insulin on maximum glucose decrease, and e) insulin dosage. The invention analyzes (for example in 1 mg/dl steps) the maximum effect of the above parameters (including the margins of error of at least the parameter of preprandial measurement) on postprandial glucose. In some preferred embodiments involving the clinically relevant range of preprandial blood glucose values (30-330 mg/dl), the system simulates the postprandial blood glucose values as outcomes according to a treatment algorithm in adult persons with diabetes. If a postprandial outcome is not normoglycemia, but turns into hyperglycemia or hypoglycemia, a critical point (CP) can be evaluated.

Any of the above-noted parameters or factors can induce a CP of postprandial blood glucose if they reach a specific margin of error. The present invention, in any of its forms, relates to glucose measurement or glucose monitoring in any tissue compartment, tissue and body fluid, e.g. interstitial fluids where such measurement or monitoring is possible. Some preferred embodiments of the present invention involve the measurement of blood glucose and, in the examples described herein, said measurement of blood glucose may be assumed unless otherwise stated.

In some embodiments, the present invention is manifested by at least one of a therapeutic tool, a diagnostic tool and an educational tool, wherein the tool(s) includes as parameters one or more of: a) preprandial measurement, b) effect of carbohydrate portions (CARB-P) on maximum glucose increase, c) patient estimate of carbohydrate amounts in food, d) effect of insulin on maximum glucose decrease, and e) insulin dosage. The tool analyzes (for example in 1 mg/dl steps) the maximum effect of the above parameters including the margins of error at least of the parameter preprandial glucose on postprandial glucose. In some preferred embodiments, one or several of the other parameters are as well considered with their margins of error. In some preferred embodiments, covering the clinically relevant range of preprandial blood glucose values (30-330 mg/dl), the tool simulates the postprandial blood glucose values as outcome according to a treatment algorithm.

In some embodiments, the present invention is further manifested by a device, e.g. a blood glucose meter, a continuous glucose monitor or an insulin pump, wherein the device operates and/or determines postprandial glucose by including as parameters one or more of: a) preprandial measurement, b) effect of carbohydrate portions (CARB-P) on maximum blood glucose increase, c) patient estimate of carbohydrate amounts in food, d) effect of insulin on maximum glucose decrease, and e) insulin dosage. The device analyzes (for example in 1 mg/dl steps) the maximum effect of the above parameters, including the margins of error at least of the parameter preprandial glucose, on postprandial glucose. In some preferred embodiment, one or several of the other parameters are as well considered with their margins of error. Covering preferably the clinically relevant range of preprandial blood glucose values (30-330 mg/dl), the device simulates the postprandial blood glucose values as outcome according to a treatment algorithm. In some embodiments, the device can then give a suggestion of treatment based on the postprandial glucose. Thus, it can help avoid reaching a critical point by giving advice and/or performing functions that avoid reaching a critical point.

The present invention is further manifested by a software program and/or a data carrier including a program that is provided with the features that it includes as parameters: a) preprandial measurement, b) effect of carbohydrate portions (CARB-P) on maximum glucose increase, c) patient estimate of carbohydrate amounts in food, d) effect of insulin on maximum glucose decrease, and/or e) insulin dosage. The program analyzes (for example in 1 mg/dl steps) the maximum effect of the above parameters including the margins of error at least of the parameter preprandial glucose on postprandial glucose. In some embodiments one or several of the parameters are considered with their margins of error. In some embodiments, the present inventon relates to or covers the clinically relevant range of preprandial blood glucose values (30-330 mg/dl). In some embodiments, the program simulates the postprandial blood glucose values as outcome according to a treatment algorithm.

In some preferred embodiments of the present invention an error is as well taken into account for one or several of:
- effect of carbohydrate-portion on maximum glucose incrase, preferably blood glucose increase,
- estimate of carbohydrate amount in meal
- the effect of prandial insulin on maximum glucose decrease, preferably blood glucose decrease, and
- insulin dosage.

In a further preferred embodiment of the present invention postprandial glucose is determined for different ranges of preprandial glucose values, in some preferred embodiments blood glucose values, according to the therapeutic scheme and the result is displayed as postprandial glucose (e.g., blood glucose) over preprandial glucose. In a further preferred embodiment it is determined whether a critical point is reached by exceeding a lower limit for glucose or by exceeding an upper limit for glucose, for example, in some preferred embodiments, blood glucose.

In some preferred embodiments, the therapeutic scheme includes a carbohydrate self-adjustment in relation to preprandial blood glucose (BG) according to the relation: BG (mg/dl): <40 40-60 61-120 121-160 161-200 201-240 241-300 301-360 CARB-P (n): X+2 X+1 X X−1 X−2 X−3 X−4 X−5 wherein X equals the number of carbohydrate portions (X=1, 2, 3, 4 or 5) for the blood glucose-range of 61-120 mg/dl.

In some embodiments, it is further preferred that the therapeutic scheme includes a preprandial insulin dose self-adjustment according to the relation:
BG (mg/dl): <61 61-80 81-120 121-160 161-200 201-240 241-300 301-360 Ins.-Dose (U): 0 −1Y Y +1Y +2Y +3Y +4Y +5Y wherein Y equals e.g. 1 unit insulin per 1 CARB-P for the blood glucose range of 81-120 mg/dl.

In some embodiments, the present invention further comprises an error grid for the evaluation of measurement errors of blood glucose meters or continuous glucose monitors.

In some embodiments, the present invention further comprises a method and/or device, e.g., a blood glucose meter, a continuous blood glucose monitor or an insulin pump, wherein on the basis of at least one result of the analysis of blood glucose at least one result, treatment information or advice is given and wherein the result or advice is given depending on the measurement error.

In some preferred embodiments of the present invention, the device is a portable device and is provided for measuring the blood glucose value of a patient. In some embodiments, the device and/or method may be adapted to display results, information or advice in a first measurement range or several first measurement ranges despite the measurement error, and may be adapted to inhibit the display of results, information or advice or display results, information or advice in a different mode in a second measurement range or in several measurement ranges depending on the measurement error. The display may be on the device or separate therefrom and may be in wire or wireless connection with the device. The device may comprise at least one movement sensor and the display may be activated or inhibited dependent on a signal from the movement sensor. In some embodiments, the device comprises or is part of a system, tool or program as described herein, or has incorporated therein a system, tool or program as described herein.

BRIEF DESCRIPTION OF THE DRAWINGS

FIG. 2 is a list of some of the parameters of a system or tool according to an embodiment of the present invention;

FIG. 3 is a table of the margins of error for the parameters of FIG. 2;

FIG. 9 is a table of parameter errors leading to a critical point in postprandial blood glucose;

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical and/or processing feature(s) of the invention, if any. In embodiments with electrical features or components, suitable electrical components and circuitry, wires, wireless components, chips, boards, software, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
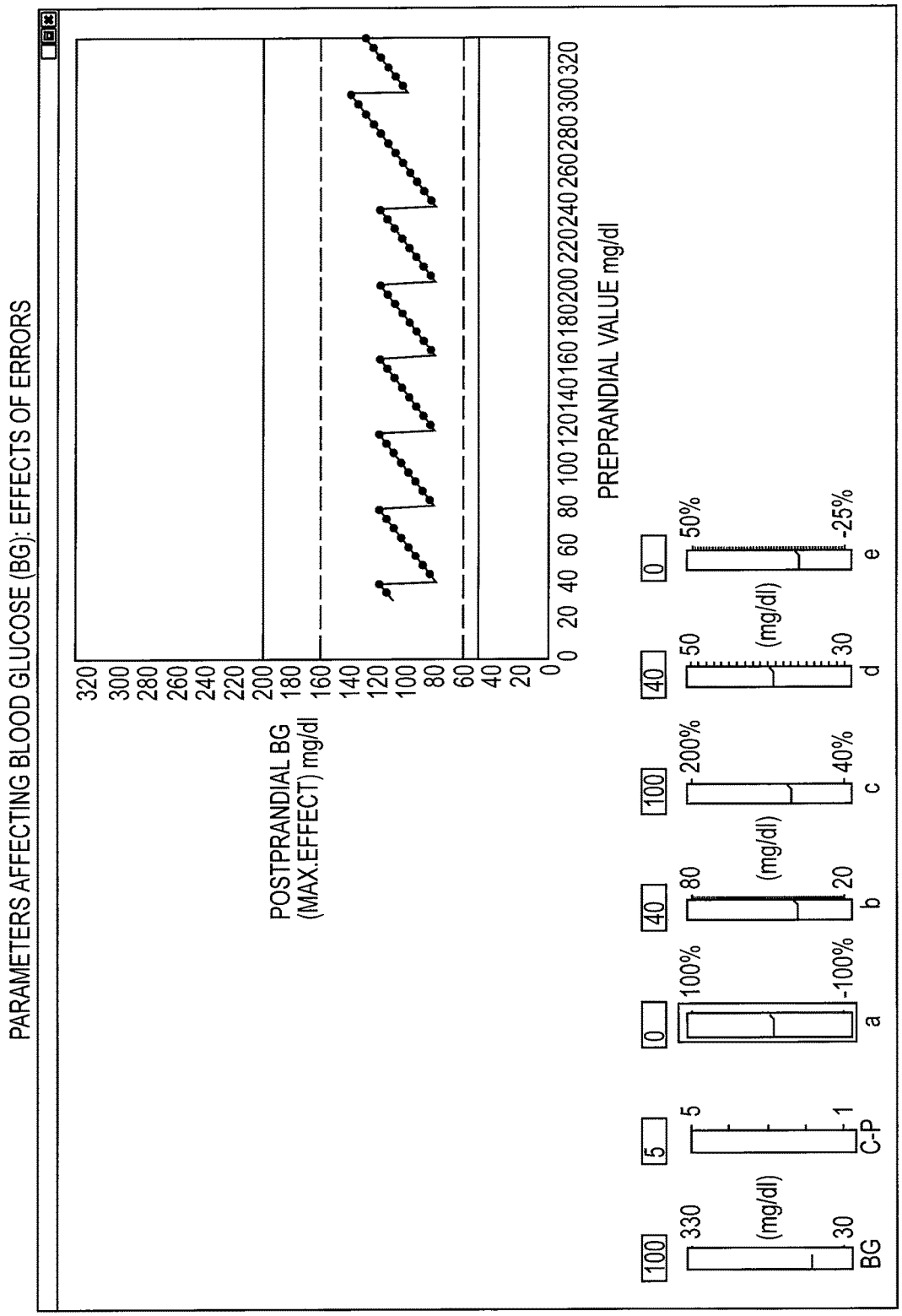
FIG. 1 shows parts of a screenshot depicting a first embodiment of the present invention.

FIG. 1 shows a screenshot of one preferred embodiment of the present invention. As explained above, the invention can be embodied as a system, a tool, a device, e.g. a glucose meter, and/or as a program. All these embodiments are encompassed when the present invention is explained in the following, and the present invention may sometimes be referred to as the or a Diabetes Error Test Model (DETM).

One preferred DETM calculates the postprandial blood glucose value. It does not show a blood glucose (BG) curve over time, but focuses mainly on the maximum effect resulting from insulin and carbohydrates consumed. However, these are not the only factors contributing to the BG result. There are numerous factors that affect the postprandial BG. The following are taken into account in the DETM and are shown in FIG. 2 as parameters that can be set. FIG. 3 shows the margins of error that are used in the present embodiment of the invention. The parameters can be set in the shown example by entering values in the fields and by moving the shown slide input means (FIG. 1). Of course, in other embodiments of the invention, for example in a device being a blood glucose meter or a continuous glucose monitor, parameters will be either measured directly, such as preprandial blood glucose or be entered via input means on the device or being stored beforehand. The parameters shown in FIGS. 1 and 2 are: a) The pre-prandial blood glucose (BG) being in the range of 30 mg/dl to 330 mg/dl which has actually been measured preprandial by a device for self-monitoring of blood glucose, for example with a strip blood glucose meter; b) the variability or effect of a carbohydrate portion, giving the blood glucose increase in mg/dl of one carbohydrate portion and being settable between 20 mg/dl and 80 mg/dl; c) the amount of carbohydrate portions the patients aims or estimates to eat (C-P) with a value of 1 to 5; d) the variability or effect of the insulin, giving the blood glucose decrease in mg/dl for a unit of insulin and being settable between 30 mg/dl and 50 mg/dl; and e) the insulin dosage.

FIG. 3 shows the margin of error for the parameters: a) the error in % with which the pre-prandial glucose concentration has been measured, with a range of −50% to +50% error (0% meaning no error); b) the error or variability of the effect of the carbohydrate effect with 45 mg/dl as normal value and an error of up to 80 mg/dl and down to 20 mg/dl; c) the error in estimating the desired amount of carbohydrate portions in % between 40% and 200% and wherein 100% means no error in estimating by the person with diabetes; d) the error or variability of the glucose concentration decrease by the insulin with a value of 40 mg/dl as errorless value and highest and lowest error values of 50 mg/dl and 30 mg/dl; and e) the error in dosing the correct amount of insulin in % and being settable between −25% and +50% wherein 0% means no error in dosing.

In one preferred embodiment, the preferred treatment algorithm used in the DETM is based on the clinical experience of the German Diabetes Research Institute/German Diabetes Centre at the Heinrich-Heine-University of Duesseldorf and can be shown in table 1 and table 2:

algorithms could be used as well but the preferred algorithm is simple to implement since it is based on addition and subtraction of carbohydrate portions and insulin units for the shown ranges of preprandial self-monitored blood glucose. The ranges can be shifted to vary the algorithm and fractions of insulin units or carbohydrate portion could be used.

The aim of the treatment algorithm is to lead the patient's BG to normoglycemia (60-160 mg/dl), whole blood. This range from 60-160 mg/dl is called target range. Of course it can be chosen to either adjust using insulin or carbohydrates for BG>120 mg/dl. As an example a calculation based on the preferred treatment algorithm can be shown as follows wherein the error of the self-monitored blood glucose is taken into account by 10% and for example additionally the errors of carbohydrate and insulin effects could be considered but are set to zero % in this calculation, so the blood glucose increase of one portion carbohydrates is 45 mg/dl and the decrease caused by the insulin is 40 mg/dl:

True BG: 120
Measurement error: 10%
Effect CARP-P: 45
Effect insulin: 40
Error: 0%
Number of carb. portions: 5 Carp-P
True BG with error (measured blood glucose): 120 mg/dl×1.1=132 mg/dl According to the treatment algorithm above 132 mg/dl leads to:

either 1 CARP-P less than intended is eaten (X−1) since the blood glucose is now in the range of 121 to 160 and thus 120 mg/dl+(4*45 mg/dl)−(5*40 mg/dl)=100 mg/dl and thus normoglycemia; or 1 additional unit insulin is administered (+1Y) if the intended carbohydrate portion is eaten since the blood glucose is now in the range of 121 to 160, and thus 120 mg/dl+(5*45)−(6*40)=105 mg/dl and thus normoglycemia.

The system, tool, device and program according to the present invention allows the calculation of the postprandial

TABLE 1

Carbohydrate Self-adjustment in relation to pre-prandial BG:

| BG (mg/dl) | <40 | 40-60 | 61-120 | 121-160 | 161-200 | 201-240 | 241-300 | 301-360 |
|---|---|---|---|---|---|---|---|---|
| CARB-P (n) | X + 2 | X + 1 | X | X − 1 | X − 2 | X − 3 | X − 4 | X − 5 |

(Base: X number of CARP-P (X = 1, 2, 3, 4 or 5) for BG-range 61-120 mg/dl)

TABLE 2

Pre-prandial Analog-Insulin Dose Self-adjustment

| BG (mg/dl) | <61 | 61-80 | 81-120 | 121-160 | 161-200 | 201-240 | 241-300 | 301-360 |
|---|---|---|---|---|---|---|---|---|
| Ins.-Dose (U) | 0 | −1Y | Y | +1Y | +2Y | +3Y | +4Y | +5Y |

(Base: Y; e.g. 1 U/1 CARB-P for BG range 81-120 mg/dl)

So, as an example of table 1 if in the blood glucose range of 61 to 120 mg/dl a carbohydrate portion X of 1 to 5 is considered, this portion value will be adjusted to X−2 when the self-monitored blood glucose value is in the range of 161 to 200 mg/dl.

As an example of table 2, one unit of insulin (Y) is considered per carbohydrate portion if the self-monitored pre-prandial blood glucose value is in the range of 81 to 120 mg/dl but is made higher by +2 units if the blood glucose value is in the range of 161 to 200 mg/dl. Other treatment blood glucose as the outcome of the pre-prandial blood glucose if the therapeutic action is taken according to the preferred algorithm (or according to another algorithm). In some preferred embodiments, the values of postprandial glucose concentration are then displayed over pre-prandial measured glucose concentration. At first, the effects of BG measurement errors are evaluated while all other parameters are kept at 0% error.

Figure 4:
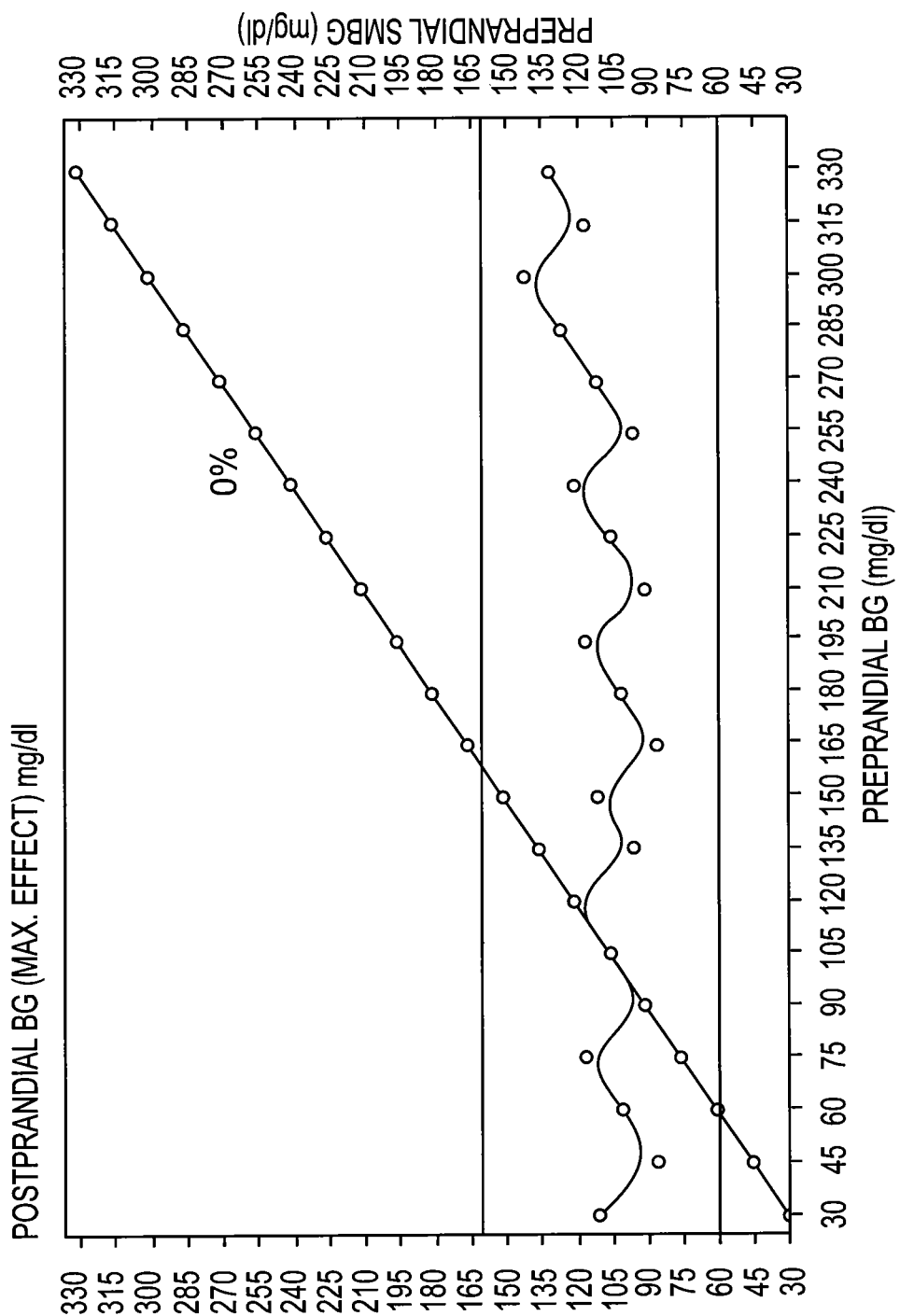
FIG. 4 is a diagram generated by an embodiment of the system, tool or program according to the present invention with zero error of all parameters.

FIG. 4 shows postprandial glucose concentration kept within the target range (shown by the horizontal lines at 60 mg/dl and 160 mg/dl postprandial glucose concentration). As an indicator for the error of the self-monitored glucose concentration the 0% error line is additionally shown which is usually not the case, so that, in some preferred embodiments, a preferred display shows only measured pre-prandial blood glucose values on the horizontal x-axis and calculated postprandial blood glucose values on the lefthand vertical y-axis.

The DETM-program can display all variables relevant in the calculation of the glucose concentration outcome in an additional window not shown in FIG. 1. Among those are the final carbohydrate portions the patients will eat after considering his current situation (C-P), the insulin he needs to apply (Y IU) and, of course, the glucose concentration result (BG_R). The "interesting" values can be checked to be displayed in a graph as, for example, shown in FIG. 4.

The graph can display the postprandial glucose concentration in relation to one changing variable. The other variables are kept constant to the set value. In some preferred embodiments, the preferred graph used most often is the shown relation between the pre-prandial (reference) glucose concentration (with values between 30 and 330 mg/dl) and the postprandial outcome.

In the graph of FIG. 4 it can be seen that with all parameters kept at 0% error all preprandial values from 30-330 mg/dl will result in postprandial values between 60 and 160 mg/dl target range). The characteristic saw tooth nature of this graph and the following graphs is a result of the stepwise nature from the treatment algorithm. In some embodiments, involving a different treatment algorithm, the resultant graph and/or display may be different from that depicted.

Figure 5:
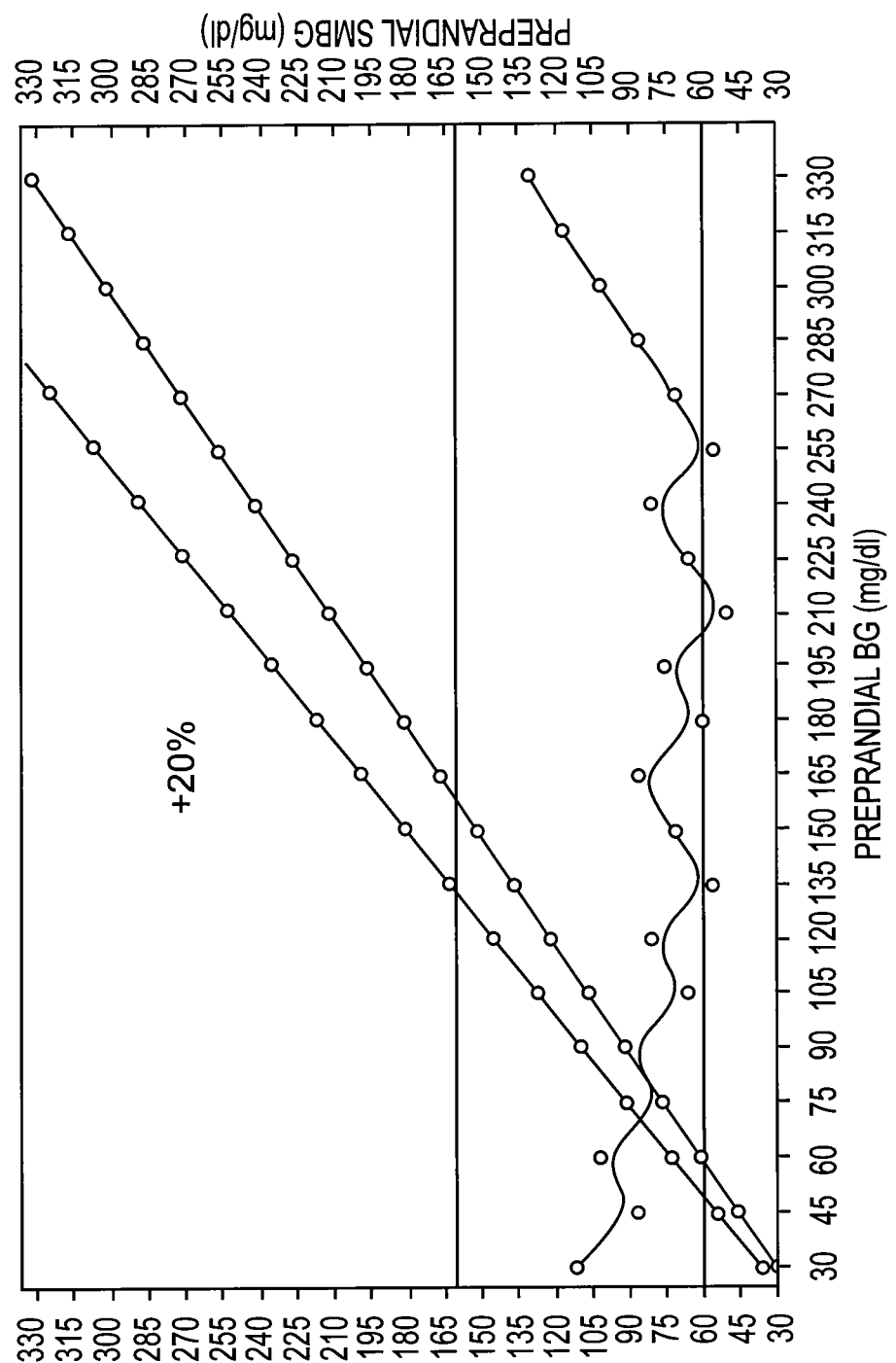
FIG. 5 is a diagram as in FIG. 4 but with a +20% error of preprandial self-monitored blood glucose.
Figure 6:
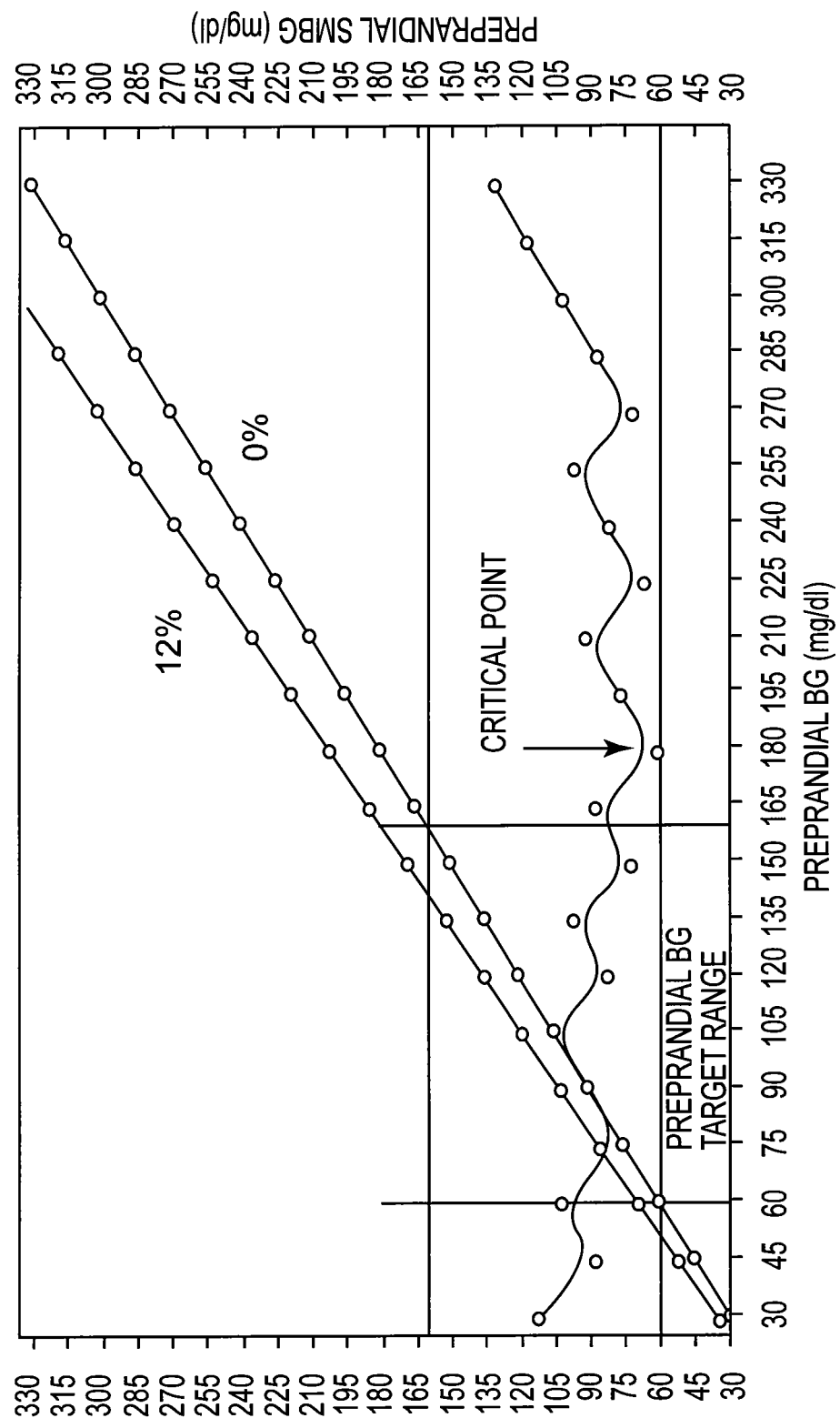
FIG. 6 is a diagram as in FIG. 5 with an error of 12% for the self-monitored blood glucose.
Figure 7:
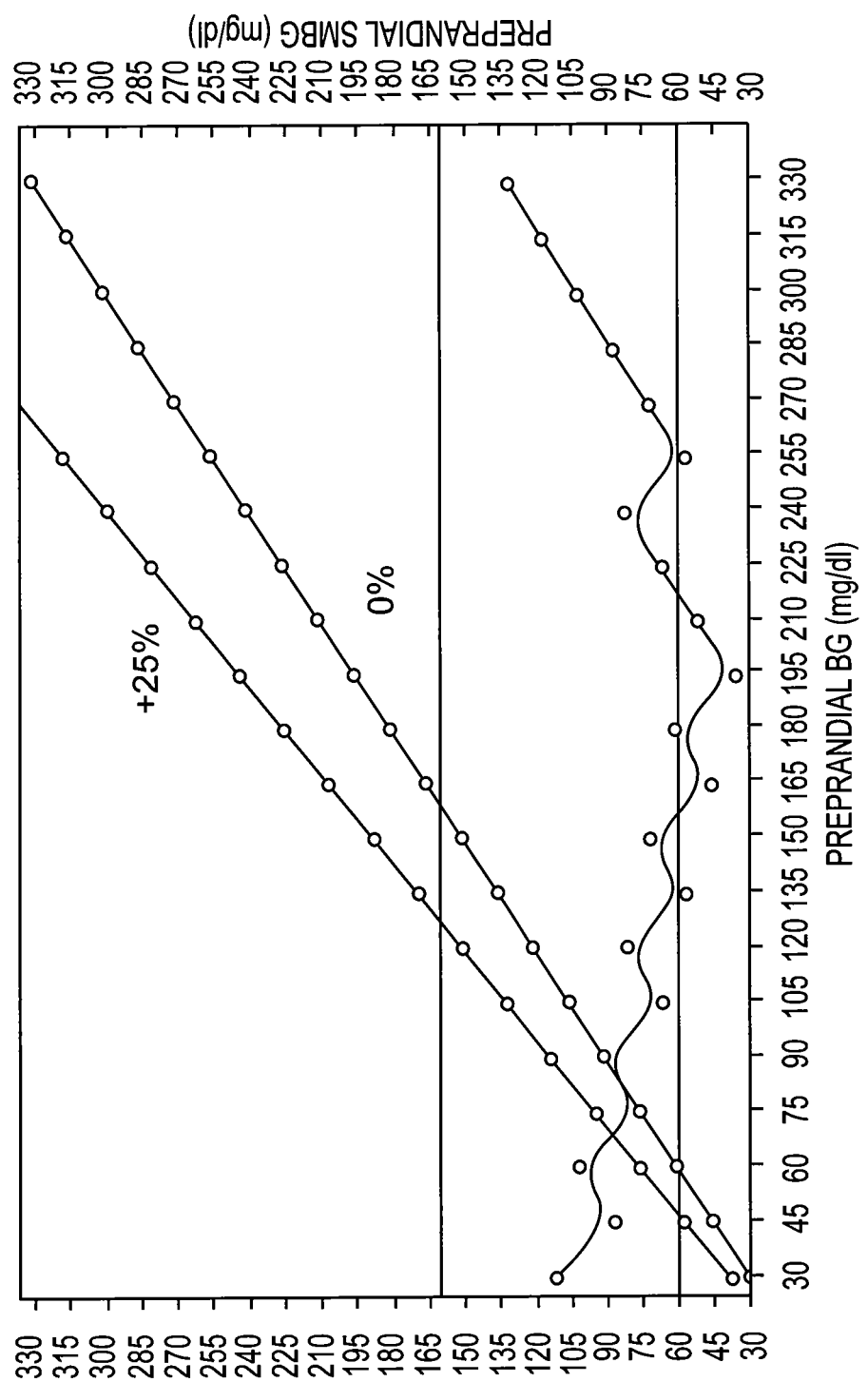
FIG. 7 is a diagram as in FIG. 5, but with an error of +25%.
Figure 8:
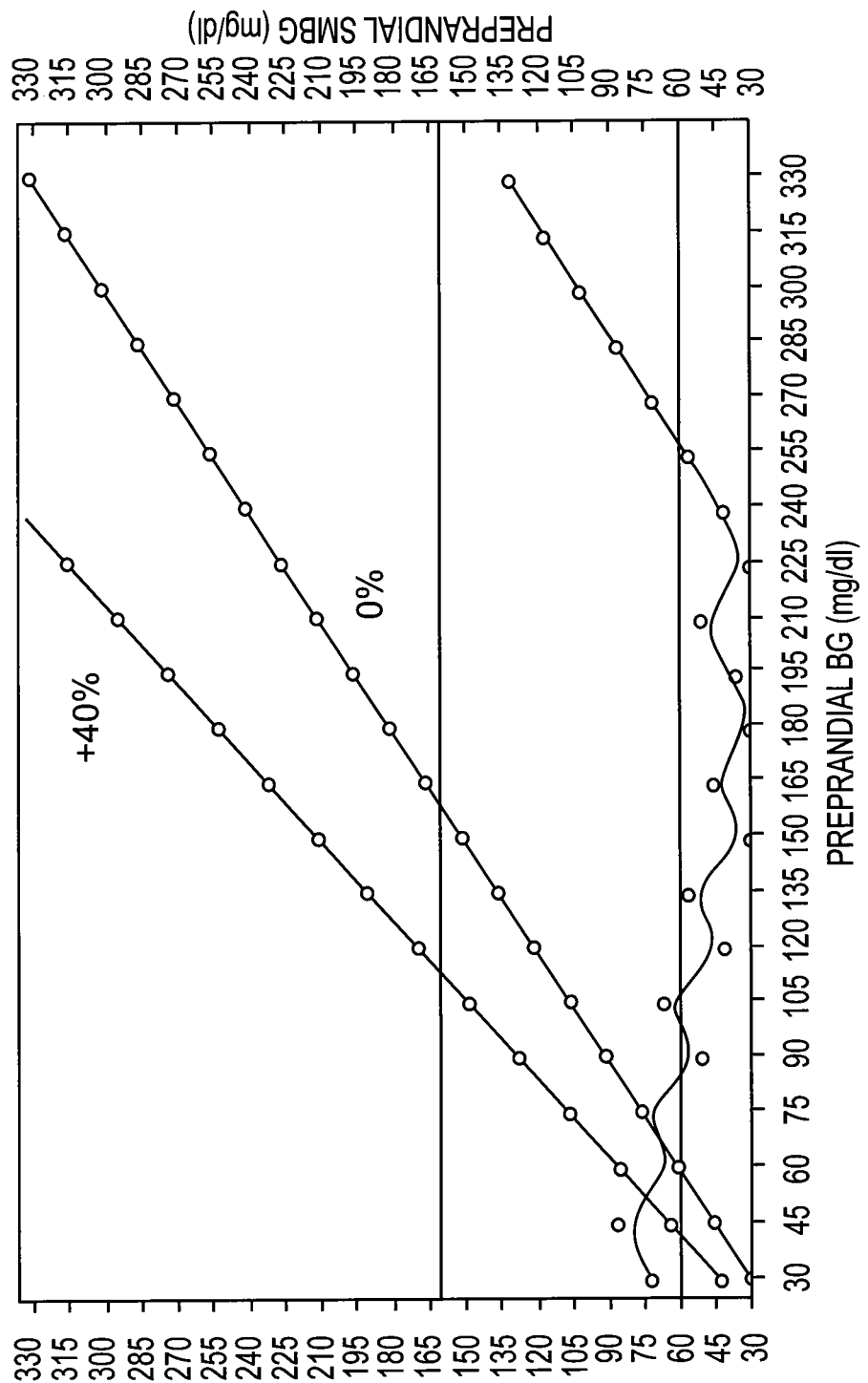
FIG. 8 is a diagram as in FIG. 5, but with an error of +40%.

FIG. 5 shows that a glucose concentration error of +20% (classified by e.g. the Error Grid Analysis (EGA) as related to zone A and thus so far as allowable, see further below) results as postprandial "outcome" in normoglycemia if preprandial glucose concentration values are in the ranges of 30-130 mg/dl and 260-330 mg/dl. However, the postprandial glucose concentration results unexpectedly in hypoglycemia if preprandial erroneous BG values are between 131 and 259 mg/dl. In this range the critical point where the target range is left for hypoglycemia is already reached at a BG measurement error of +12% as can be shown in FIG. 6. Thus, a device such as a blood glucose meter or an insulin pump will be able to display useful values or therapeutic advice if the preprandial values are in the range of 30-130 mg/dl and will act accordingly while on the other hand such a device will inhibit the display of results in the range of 131-259 mg/di or will inhibit displaying therapeutical advice or will give a warning. FIGS. 7 and 8 show postprandial glucose values for other error percentages of the self-monitored glucose.

FIG. 7 shows the postprandial blood glucose to decrease into hypoglycemia due to a preprandial self-monitored glucose measurement with an error of +25% (with all other errors of the system kept to 0%). FIG. 8 shows a decrease into hypoglycemia due to a preprandial error of 40%.

The DETM system, tool, device and program provide for and/or allow the characterization of the relevance of errors of parameters affecting BG on postprandial BG outcome. It describes in detail the effects of potential errors of parameters affecting glucose concentration on postprandial glucose values within the clinically relevant glucose range. It evaluates the clinical relevance of these errors and presents a detailed risk assessment with the focus on postprandial outcome. In some preferred embodiments, it is therefore preferably used in or as an educational tool(s) for explaining the relations to people with diabetes. In some preferred embodiments, it is used in devices for diabetes care. For example, when used in a blood glucose meter, the system, tool or program will know the measurement error of the device and can therefore calculate the postprandial blood glucose and can give a warning if a critical point is reached. The device can further give a corrected treatment advice or information if it detects that, based on the self-monitored blood glucose value, the error and other parameters, a critical point would be reached for the postprandial blood glucose value.

The Critical Point (CP): A Critical Point is reached if (preprandial) normoglycemia turns into (postprandial) hypo- or hyperglycemia or (preprandial) hyperglycemia turns into (postprandial) hypoglycemia or (preprandial) hypoglycemia turns into (postprandial) hyperglycemia. For example if the glucose measurement error is 11% this leads for the preprandial glucose value of 219 mg/dl to a postprandial value of 59 mg/dl (outside the target range). As 11% is the lowest value for the glucose measurement error to result in at least one value outside the target range this is called the Critical Point. FIG. 9 shows a table of critical points reached by parameter errors.

The treatment algorithm can be extended to Continuous Glucose Monitoring (CGM). The following assumptions are made for possible glucose changes:

| Very Fast glucose increase | >+2 mg/dl/min | UU |
| Fast | +(1-2) mg/dl/min | U |
| Slow changes | <±1 mg/dl/min | = |
| Fast decrease | -(1-2) mg/dl/min | D |
| Very Fast decrease | >-2 mg/dl/mim | DD |

| | glucose-Trend (mg/dl/min) | | | glucose-Change(mg/dl) in 30 minutes | |
|---|---|---|---|---|---|
| | mean | range | | mean | range |
| UU | +3.0 | +(2.1→3.9) | → | +45 | +(31→59) |
| U | +1.5 | +(1.0→2.0) | → | +23 | +(15→30) |
| = | ±0 | -0.9→+0.9 | → | ±0 | -14→+14 |
| D | -1.5 | -(1.0→2.0) | → | -23 | -(15→30) |
| DD | -3.0 | -(2.1→3.9) | → | -45 | -(31→59) |

This leads to the following treatment algorithms for adapting the insulin units:

| | Glucose (mg/dl) | | | | | | | |
|---|---|---|---|---|---|---|---|---|
| Trend | <61 | 61-80 | 81-120 | 121-160 | 161-200 | 201-240 | 241-300 | 301-360 |
| UU | 0 | Y | +1Y | +2Y | +3Y | +4Y | +5Y | +6Y |
| U | 0 | −1Y | Y | +1Y | +2Y | +3Y | +4Y | +5Y |
| = | 0 | −1Y | Y | +1Y | +2Y | +3Y | +4Y | +5Y |
| D | 0 | −2Y | −1Y | Y | +1Y | +2Y | +3Y | +4Y |
| DD | 0 | −3Y | −2Y | −1Y | Y | +1Y | +2Y | +3Y |

In the DETM-program, tool, system or device the CGM-algorithms can be used for any calculation made. In particular, the device in this case of algorithm is a continuously measuring glucose monitor.

Figure 10:
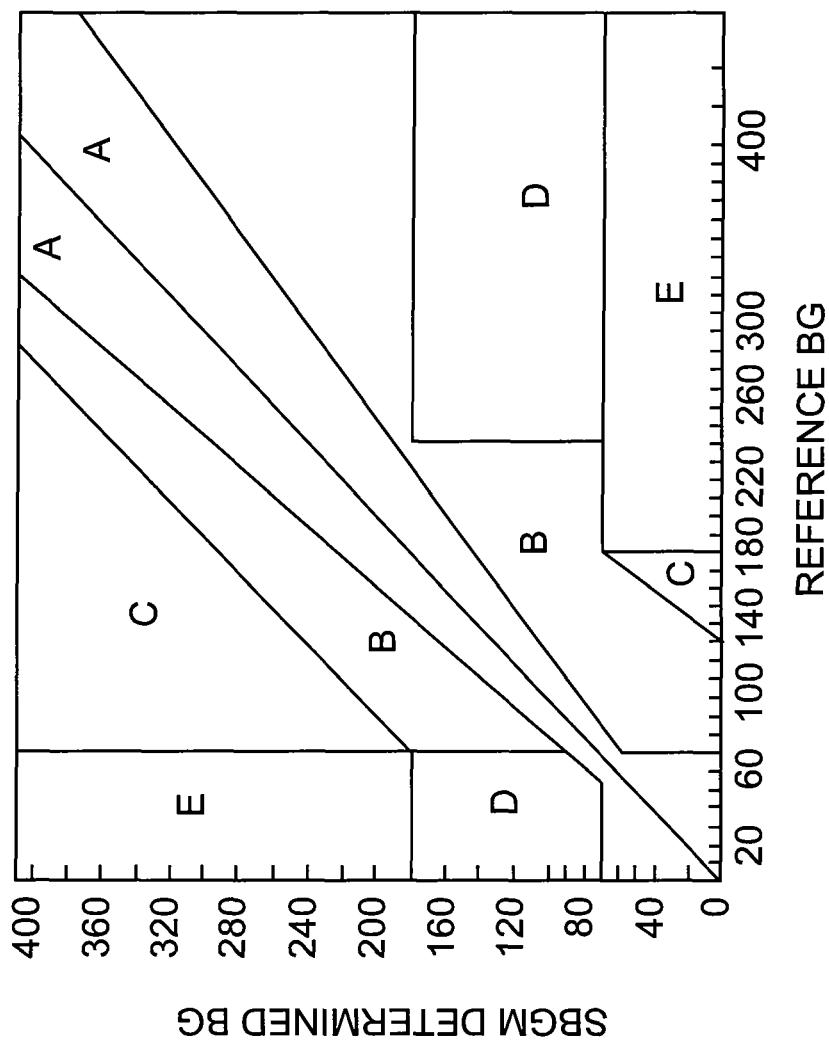
FIG. 10 depicts a known error grid model for judging acceptance of measurement errors.

Another aspect of the present invention is that by using the DETM model and algorithms, an error grid model similar to the EGA can be calculated, called hereinafter the EAA. FIG. 10 shows the EGA as known. [Joan L. Parkes, Scott Pardo, Stephen 1. Slatin, Barry H. Ginsberg, "A new consensus Error Grid to evaluate the clinical significance of inaccuracies in the measurement of blood glucose", Diabetes Care, Vol 23, No. 8, pages 1143-1148, August 2000].

In some preferred embodiments, by using the DETM system, tool and program with preferred algorithms, an error grid model comparable to the EGA can be calculated.

The target range is amended with an acceptance range (50-200 mg/dl); the target range is the equivalent to EGA zone A; the acceptance range is the equivalent to EGA zone B; for the EAA it is calculated which measurement error at which pre-prandial glucose value leads to a post-prandial BG value outside the target/acceptance range.

Figure 11:
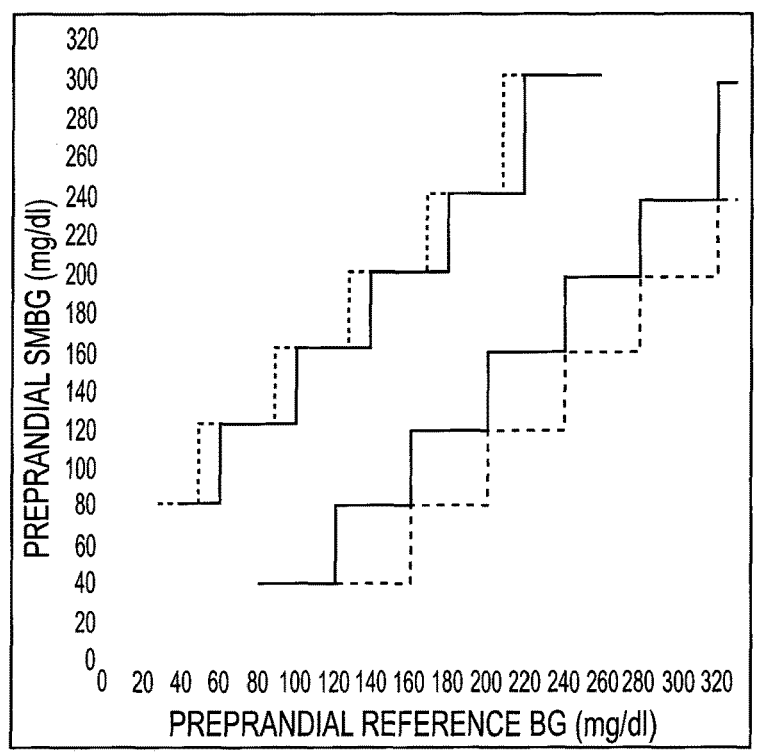
FIG. 11 depicts a new error grid model in accordance with the present invention.
Figure 12:
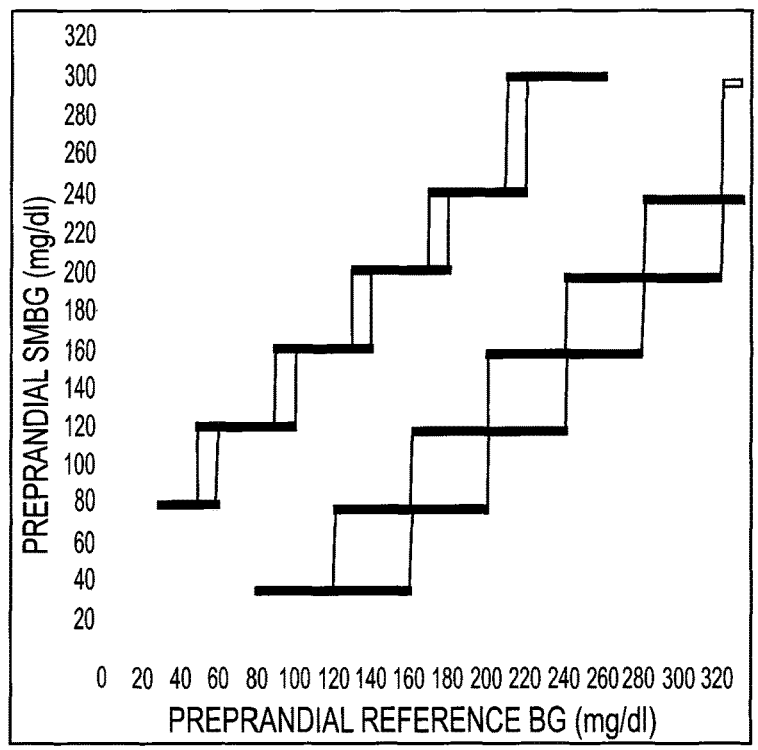
FIG. 12 depicts the new error grid model used to measure the quality of blood glucose measurements.

The result is a relation between preprandial reference glucose and preprandial self-monitored glucose as shown in FIG. 11. The full lines represent the target range, the dotted lines the acceptance range. The EAA can now be used to measure the quality of glucose measurements by projecting the reference value and self-measurement value into the grid as shown in FIG. 12. Points outside the full/dotted lines mean that if a patient measured this value (with the corresponding reference value) his/her glucose concentration would result in hypo/hyperglycemia after applying his treatment algorithm. In this figure most of the points lie between the lines, but several points are outside (above). This means that using this glucose meter, the patient is in danger of ending up in hypoglycemia.

Figure 13:
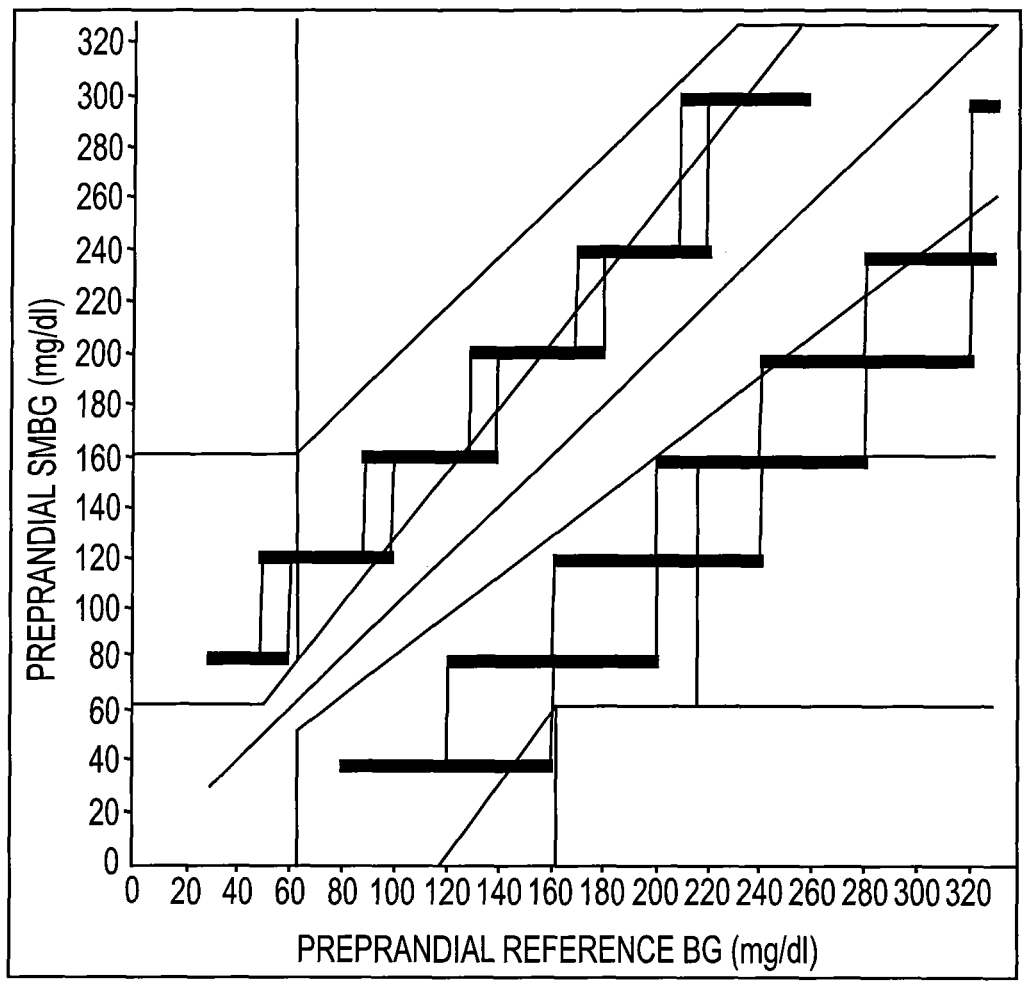
FIG. 13 depicts the new error grid model in comparison with the known EGA model

In order to evaluate the exact risk, the system, tool and program in accordance with the present invention offers the option of calculating both EAA and EGA as shown in FIG. 13. In this calculation it can be seen that 9% of the points are outside the acceptance range. Interestingly, no point is outside zone A of the EGA. This means that, according to the EGA, this measurement device is perfect, while according to the EAA it is unusable. The EGA can be painted into the EAA as shown to provide an optical visualization.

Notes and considerations: the DETM and treatment algorithms are calibrated to whole blood. Nevertheless the system, tools, devices and the program in accordance with the present invention may offer the option of switching to plasma. The DETM focuses on the BG-outcome after food intake and insulin administration (with several side effects).

The EAA focuses on evaluating the quality of a measurement device. This quality depends on the treatment algorithm used (which can be adapted in the DETM-program) Continuous glucose monitoring is implemented using slight modifications to the standard treatment algorithm without breaking the scheme Any or all parameters and/or features associated with the present invention can be combined. This means that, for example, all EAA calculations can be performed for higher insulin impact then usual.

In some preferred embodiments, the DETM-program has a database or memory operably coupled, linked or attached so that results from tests of measurement devices can be stored, selected and/or transmitted easily.

The measurement error of an analytical system such as a blood glucose meter or a continuous glucose monitor influences the usefulness and significance of the analytical result. If the measured glucose value is outside of a physiologically preferable concentration, a therapeutic action is initiated with the aim of restoring the physiologically preferred state. In case of diabetes mellitus therapeutical interventions such as administering insulin or carbohydrates are taken to bring the concentration of glucose back to normoglycemia. The analytical result can be displayed or otherwise presented as numerical value or as therapeutic advice based on the measurement which can be a single measurement or a measurement and a consideration of earlier measurements as in continuous glucose monitoring.

The therapeutic intervention depends on the concentration or concentration range of the glucose value and the target range for normoglycemia. In the present invention the display or presentation of therapeutic advice or information is made dependent on the outcome of the glucose value (e.g. the postprandial value) which, on the other hand, depends on the error of the measurement as explained above. In particular, in some embodiments advice is given or information communicated only if the above explained system, tool or program detects that postprandial glucose is within the target range for the actual measurement range.

Accordingly, since the display of a measured value or advice, e.g., therapeutic advice, is given under consideration of the measurement error and its relevance for the later reached blood glucose value, it is possible to communicate or present therapeutic advice or a measurement display that is informative and correct for the user. It can be taken into account by the device that a measurement is within a range that allows advice to be presented or communicated despite the measurement error or is within a range that leads to a critical point so that no advice or modified advice has to be given.

An advantage of the present invention is therefore that in those ranges of glucose where correct therapy advice can be given despite a large measurement error such advice will be given. On the other hand, in those ranges where it is necessary to have a low error for giving a correct therapy advice such advice can be inhibited or modified or replaced by a warning. The display may be presented or communicated in any suitable form, e.g. either directly on a device, or by wireless (infrared, radiofrequencies) or wirebound data connection with a device.

For example, if the device is a continuously monitoring glucose device that reacts on movements of the wearer in such a way that movements may increase the measurement error, it may be preferred to have a movement sensor included in the device so that the error by movement can be included in the above explained calculation by adding a further error parameter.

While preferred embodiments of the present invention are shown and described, it should be understood that the invention is not limited thereto but may be otherwise variously embodied and practiced within the scope of the following claims.

The invention claimed is:

1. A device for determining a postprandial blood glucose concentration for a person with diabetes which takes into account factors or variables in a treatment of the diabetes, the device being one of a blood glucose meter comprising a strip measurement device, a continuous glucose monitor, or an insulin pump comprising:
    a processor adapted to execute computer implemented instructions to provide at least one of a result, advice, and information regarding a determined postprandial blood glucose concentration for the person with diabetes, based on at least one result of an analysis of glucose, and wherein the processor is further adapted to execute computer implemented instructions to determine whether to display said at least one of a result, advice, and information based at least in part on an effect of measurement errors on the determined postprandial blood glucose concentration and associated with at least two of:
    a preprandial glucose concentration measurement by self-monitoring of glucose;
    an effect of carbohydrate-portion on maximum glucose increase;
    an estimate of carbohydrate amount in a meal;
    an effect of prandial insulin on maximum glucose decrease; and
    an insulin dosage;
    wherein when the determined postprandial blood glucose concentration including the effect of measurement errors is in a range indicative of normoglycemia, the processor is adapted to execute computer implemented instructions to display said at least one of a result, advice, and information; and
    wherein when the determined postprandial blood glucose concentration including the effect of measurement errors is outside a range indicative of normoglycemia such that a critical point is reached indicative of one of hypoglycemia and hyperglycemia, the processor is adapted to execute computer implemented instructions to display a warning, a corrected treatment advice, or corrected information.

2. The device of claim 1, wherein the device is portable and is provided for measuring the glucose value of a patient.

3. The device according to claim 1, wherein the processor is further adapted to execute computer implemented instructions to display the result, advice and information in a first measurement range or several first measurement ranges, and to inhibit the display of the result, advice and information in a second measurement range or in several second measurement ranges.

4. The device according to claim 1, further comprising an operably coupled display in one of wired or wireless connection with the blood glucose meter, the continuous glucose monitor, or the insulin pump.

5. The device according to claim 4, further comprising at least one movement sensor wherein the display may be activated or inhibited dependent on a signal from the movement sensor.

6. The device according to claim 1, wherein one of the measurement error is at least a margin of error for the self-monitored preprandial glucose and wherein the processor is further adapted to execute computer implemented instructions to calculate postprandial glucose values based on a therapeutic action scheme.

7. The device according to claim 6, wherein the postprandial glucose values are determined for different ranges of preprandial glucose concentration values according to the therapeutic scheme.

8. The device according to claim 7, wherein the processor is further adapted to execute computer implemented instructions to display as a result postprandial blood glucose over preprandial blood glucose.

9. The device according to claim 6, wherein the blood glucose meter or the continuous glucose monitor is adapted for glucose measurement or glucose monitoring in blood or any tissue compartment, tissues, body fluid or interstitial fluid.

10. The device according to claim 1, wherein the processor is further adapted to execute computer implemented instructions to calculate postprandial glucose values based on a therapeutic action scheme.

11. A device for determining a postprandial blood glucose concentration for a person with diabetes which takes into account factors or variables in a treatment of the diabetes, the device being one of a blood glucose meter comprising a strip measurement device, a continuous glucose monitor, or an insulin pump comprising:
    a processor adapted to execute computer implemented instructions to provide at least one of a result, advice, and information regarding a determined postprandial blood glucose concentration for the person with diabetes based on at least one result of an analysis of glucose;
    wherein the processor is further adapted to execute computer implemented instructions to provide said at least one of a result, advice, and information based on at least one of:
        a preprandial glucose concentration measurement by self-monitoring of glucose;
        an effect of carbohydrate-portion on maximum glucose increase;
        an estimate of carbohydrate amount in a meal;
        an effect of prandial insulin on maximum glucose decrease; and
        an insulin dosage;
    wherein the processor is further adapted to execute computer implemented instructions to determine whether to display said at least one of a result, advice, and information based at least in part on an effect of measurement errors on the determined postprandial blood glucose concentration and associated with a preprandial glucose concentration measurement by self-monitoring of glucose and at least one of:
    an effect of carbohydrate-portion on maximum glucose increase;
    an estimate of carbohydrate amount in a meal;
    an effect of prandial insulin on maximum glucose decrease; and
    an insulin dosage;
    wherein the processor is further adapted to execute computer implemented instructions to, display said at least one of a result, advice and information when the determined postprandial blood glucose concentration including the effect of measurement errors is in a first measurement range or several first measurement ranges indicative of normoglycemia, and to inhibit the display of the result, advice and information when the determined postprandial blood glucose concentration including the effect of measurement errors is in a second measurement range or in several second measurement ranges outside a range indicative of normoglycemia such that a critical point is reached indicative of one of hypoglycemia and hyperglycemia and display a warning, a corrected treatment advice, or corrected information; and wherein the processor is further adapted to execute computer implemented instructions to calculate postprandial glucose values based on a therapeutic action scheme.

12. The device according to claim 10, wherein the therapeutic action scheme includes a carbohydrate self-adjustment in relation to preprandial blood glucose (BG).

13. The device according to claim 10, wherein the therapeutic scheme includes a preprandial insulin dose self-adjustment.

14. A device for determining a postprandial blood glucose concentration for a person with diabetes which takes into account factors or variables in a treatment of the diabetes, the device being one of a blood glucose meter comprising a strip measurement device, a continuous glucose monitor, or an insulin pump comprising:

a processor adapted to execute computer implemented instructions to provide at least one of a result, advice, and information regarding a determined postprandial blood glucose concentration for the person with diabetes, and wherein the processor is further adapted to execute computer implemented instructions to determine whether to display said at least one of a result, advice, and information based at least in part on an effect of measurement errors on the determined postprandial blood glucose concentration and associated with a preprandial glucose concentration measurement by self-monitoring of glucose, and an error associated with at least one of:

an effect of carbohydrate-portion on maximum glucose increase;

an estimate of carbohydrate amount in a meal;

an effect of prandial insulin on maximum glucose decrease; and an insulin dosage;

wherein when the determined postprandial blood glucose concentration including the effect of measurement errors is in a range indicative of normoglycemia, the processor is adapted to execute computer implemented instructions to display said at least one of a result, advice, and information; and wherein when the determined postprandial blood glucose concentration including the effect of measurement errors is outside a range indicative of normoglycemia such that a critical point is reached indicative of one of hypoglycemia and hyperglycemia, the processor is adapted to execute computer implemented instructions to display a warning, a corrected treatment advice, or corrected information.

15. An improved graphical user interface (GUI) display on an electronic device with a memory and a processor to execute one or more programs stored in memory for determining a postprandial blood glucose concentration for a person with diabetes which takes into account factors or variables in a treatment of the diabetes, the electronic device being one of a blood glucose meter comprising a strip measurement device, a continuous glucose monitor, or an insulin pump, the improved GUI display comprising:

at least one of a result, advice, and information displayed in response to a determined postprandial blood glucose concentration including the effect of measurement errors being in a range indicative of normoglycemia; and at least one of a warning, a corrected treatment advice, or corrected information displayed in place of said at least one of a result, advice, and information in response to the determined postprandial blood glucose concentration including the effect of measurement errors being outside a range indicative of normoglycemia such that a critical point is reached indicative of one of hypoglycemia and hyperglycemia such that said at least one of a result, advice, and information is incorrect;

wherein the processor is adapted to execute computer implemented instructions to:

determine a determined postprandial blood glucose concentration for the person with diabetes, based on at least one result of an analysis of glucose;

determine an effect of measurement errors on the determined postprandial blood glucose concentration, the measurement errors associated with at least two of:

a preprandial glucose concentration measurement by self-monitoring of glucose;

an effect of carbohydrate-portion on maximum glucose increase;

an estimate of carbohydrate amount in a meal;

an effect of prandial insulin on maximum glucose decrease; and an insulin dosage;

determine said at least one of a result, advice, and information regarding the determined postprandial blood glucose concentration including the effect of measurement errors to display in response to the determined postprandial blood glucose concentration including the effect of measurement errors being in a range indicative of normoglycemia; and determine said at least one of a warning, a corrected treatment advice, or corrected information to display in response to the determined postprandial blood glucose concentration including the effect of measurement errors being outside of the range indicative of normoglycemia such that a critical point is reached indicative of one of hypoglycemia and hyperglycemia.

* * * * *